(12) United States Patent
Kawano

(10) Patent No.: US 9,968,243 B2
(45) Date of Patent: May 15, 2018

(54) GUIDING DEVICE FOR CHANGING MAGNETIC FIELD TO CHANGE RESTRAINED POSITION FOR RESTRAINING CAPSULE MEDICAL DEVICE RELATIVE TO POSITION OF CAPSULE MEDICAL DEVICE, AND CAPSULE MEDICAL DEVICE GUIDING SYSTEM

(71) Applicant: OLYMPUS CORPORATION, Tokyo (JP)

(72) Inventor: Hironao Kawano, Machida (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days. days.

(21) Appl. No.: 15/254,099

(22) Filed: Sep. 1, 2016

(65) Prior Publication Data
US 2016/0367121 A1 Dec. 22, 2016

Related U.S. Application Data

(63) Continuation of application No. PCT/JP2015/062659, filed on Apr. 27, 2015.

(30) Foreign Application Priority Data

Aug. 20, 2014 (JP) .................................. 2014-167963

(51) Int. Cl.
*A61B 1/00* (2006.01)
*A61B 5/06* (2006.01)
(Continued)

(52) U.S. Cl.
CPC ................ *A61B 1/041* (2013.01); *A61B 1/00* (2013.01); *A61B 1/00158* (2013.01);
(Continued)

(58) Field of Classification Search
CPC . A61B 1/041; A61B 1/00158; A61B 1/00006; A61B 5/062; A61B 5/061;
(Continued)

(56) References Cited

U.S. PATENT DOCUMENTS

2008/0300458 A1 12/2008 Kim et al.
2009/0093678 A1* 4/2009 Kimura .............. A61B 1/00158
600/117

(Continued)

FOREIGN PATENT DOCUMENTS

CN 101801254 A 8/2010
JP 2008-503310 A 2/2008
(Continued)

OTHER PUBLICATIONS

International Search Report dated Jul. 21, 2015 issued in PCT/JP2015/062659.
(Continued)

*Primary Examiner* — John P Leubecker
(74) *Attorney, Agent, or Firm* — Scully, Scott, Murphy & Presser, P.C.

(57) ABSTRACT

A guiding device is configured to guide a capsule medical device within a subject by means of a magnetic field. The guiding device includes a magnetic field generating unit configured to generate the magnetic field to define a specific position where the capsule medical device is restrained on an arbitrary horizontal plane, a position detecting unit configured to detect a position of the capsule medical device in the subject to output positional information, and a control unit configured to: compare a distance between the specific position and the capsule medical device with a first threshold value based on the positional information; and control the magnetic field generating unit to change distribution of the magnetic field relative to the capsule medical device so as to
(Continued)

bring the specific position close to a position of the capsule medical device when the distance is determined to be greater than the first threshold value.

10 Claims, 12 Drawing Sheets

(51) Int. Cl.
    *A61B 1/04*     (2006.01)
    *A61B 5/00*     (2006.01)
    *A61B 5/145*     (2006.01)

(52) U.S. Cl.
    CPC ............ *A61B 5/0084* (2013.01); *A61B 5/062* (2013.01); *A61B 5/6861* (2013.01); *A61B 5/14539* (2013.01); *A61B 2560/0219* (2013.01)

(58) Field of Classification Search
    CPC ................ A61B 5/0084; A61B 5/6861; A61B 2034/731; A61B 2034/733; A61B 2034/2051
    See application file for complete search history.

(56) References Cited

U.S. PATENT DOCUMENTS

2009/0253999 A1* 10/2009 Aoki .................. A61B 1/00016
    600/565
2010/0168516 A1   7/2010 Uchiyama
2010/0179782 A1*   7/2010 Kimura .............. A61B 1/00158
    702/94
2011/0184690 A1*   7/2011 Iida .................... A61B 1/00158
    702/150
2011/0196202 A1*   8/2011 Kimura .............. A61B 1/00158
    600/109
2011/0292196 A1   12/2011 Kawano
2012/0098523 A1*   4/2012 Iida .................... A61B 1/00158
    324/202
2012/0149981 A1*   6/2012 Khait ................ A61B 1/00158
    600/109
2014/0148643 A1   5/2014 Kawano

FOREIGN PATENT DOCUMENTS

WO   WO 2011/055578 A1   5/2011
WO   WO 2013/168681 A1   11/2013

OTHER PUBLICATIONS

Keller, H. et al., "Method for Navigation and Control of a Magnetically Guided Capsule Endoscope in the Human Stomach", Biomedical Robotics and Biomechatronics, 2012 4th IEEE RAS & EMBS International Conference on Biomedical Robotics and Biomechatronics, Jun. 24-27, 2012, pp. 859-865.
Extended Supplementary European Search Report dated Feb. 28, 2018 in European Patent Application No. 15 83 3787.3.

* cited by examiner

GUIDING DEVICE FOR CHANGING MAGNETIC FIELD TO CHANGE RESTRAINED POSITION FOR RESTRAINING CAPSULE MEDICAL DEVICE RELATIVE TO POSITION OF CAPSULE MEDICAL DEVICE, AND CAPSULE MEDICAL DEVICE GUIDING SYSTEM

CROSS REFERENCES TO RELATED APPLICATIONS

This application is a continuation of PCT international application Ser. No. PCT/JP2015/062659, filed on Apr. 27, 2015 which designates the United States, incorporated herein by reference, and which claims the benefit of priority from Japanese Patent Application No. 2014-167963, filed on Aug. 20, 2014, incorporated herein by reference.

BACKGROUND

1. Technical Field

The disclosure relates to a guiding device and a capsule medical device guiding system for guiding a capsule medical device introduced into a subject.

2. Related Art

Conventionally, a capsule medical device has been developed that is configured to be introduced into a subject to obtain various kinds of information about the inside of the subject, or to administer a medical agent or the like into the subject. For example, in the field of endoscopes, a capsule endoscope formed to have such a size as to allow itself to be introduced into a digestive tract of a subject is known.

The capsule endoscope includes an imaging function and a wireless communication function inside a capsule-shaped casing. The capsule endoscope is swallowed by a subject and performs imaging while moving through the inside of a digestive tract by means of peristaltic movement or the like. The capsule endoscope then sequentially and wirelessly transmits image data of images of the inside of an organ of the subject (hereinafter also referred to as an in-vivo image). The wirelessly transmitted image data are received by a receiving device provided outside the subject and obtained by an image display device such as a workstation to be subjected to a predetermined image process. Consequently, the in-vivo image of the subject can be displayed on a screen of the image display device in the form of a still image or a motion image.

In recent years, a guiding system including a guiding device has been proposed (for example, refer to Japanese Translation of PCT International Application Publication No. JP-T-2008-503310). Specifically, the guiding device guides, by means of a magnetic field, a capsule endoscope introduced into a subject. In such a guiding system, generally, a permanent magnet is provided inside the capsule endoscope, and a magnetic field generation unit such as an electromagnet and a permanent magnet is provided in the guiding device. A liquid such as water is then introduced into a digestive tract of the subject such as a stomach, and the capsule endoscope is caused to float in the liquid. In this state, the capsule endoscope inside the subject is guided by a magnetic field generated by the magnetic field generation unit. The guiding system is provided with a display unit that receives image data obtained by the capsule endoscope and displays an in-vivo image. This allows a user to operate the guidance for the capsule endoscope using an operation input unit provided on the guiding device with reference to the in-vivo image displayed on the display unit.

SUMMARY

In some embodiments, a guiding device is configured to guide a capsule medical device within a subject by means of a magnetic field. The guiding device includes: a magnetic field generating unit configured to generate the magnetic field to define a specific position where the capsule medical device is restrained on an arbitrary horizontal plane; a position detecting unit configured to detect a position of the capsule medical device in the subject to output positional information; and a control unit configured to: compare a distance between the specific position and the capsule medical device with a first threshold value based on the positional information; and control the magnetic field generating unit to change distribution of the magnetic field relative to the capsule medical device so as to bring the specific position close to a position of the capsule medical device when the distance is determined to be greater than the first threshold value.

In some embodiments, a capsule medical device guiding system includes the guiding device and the capsule medical device.

The above and other features, advantages and technical and industrial significance of this invention will be better understood by reading the following detailed description of presently preferred embodiments of the invention, when considered in connection with the accompanying drawings.

DETAILED DESCRIPTION

Hereinafter, a guiding device and a capsule medical device guiding system according to some embodiments of the present invention will be described with reference to the drawings. In the following description, a capsule endoscope that is orally introduced into a subject to capture the inside of a digestive tract of the subject is described as an example of a capsule medical device to be guided by the capsule medical device guiding system according to the present embodiment. However, the present invention is not limited by this embodiment. In other words, the present invention can be applied to guidance for various capsule-shaped medical devices such as, for example, a capsule endoscope that moves through the inside of a lumen ranging from an esophagus to an anus of a subject, a capsule medical device that delivers a medical agent or the like into a subject, and a capsule medical device including a pH sensor that measures pH within a subject.

In the following description, a shape, a size, and a positional relation are only schematically illustrated in each drawing to such an extent that contents of the present invention can be understood. Therefore, the present invention is not limited only to the shape, the size, and the positional relation represented in each drawing. The same reference signs are used to designate the same elements throughout the drawings.

Embodiments

Figure 1:
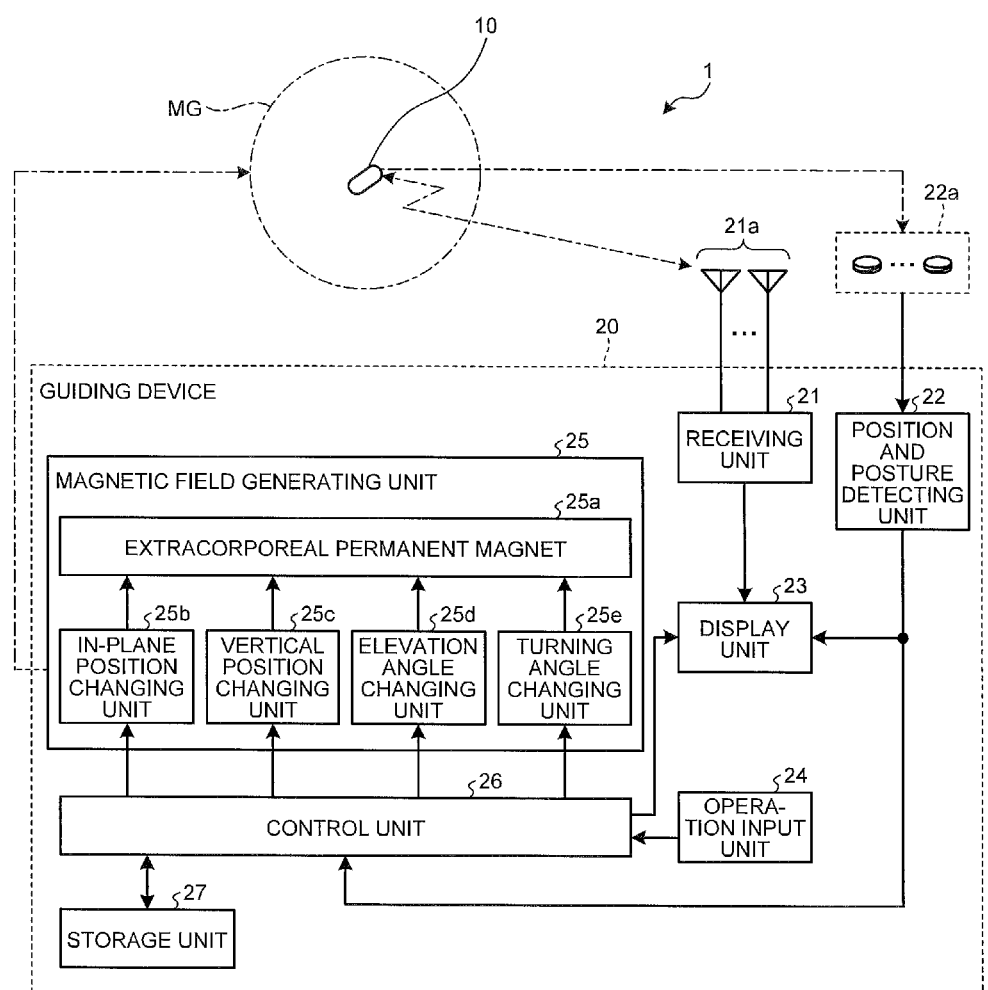
FIG. 1 is a diagram illustrating an exemplary configuration of a capsule medical device guiding system according to an embodiment of the present invention.

FIG. 1 is a diagram illustrating an exemplary configuration of a capsule medical device guiding system according to an embodiment of the present invention. As illustrated in FIG. 1, the capsule medical device guiding system 1 according to the present embodiment includes a capsule endoscope 10 and a guiding device 20. The capsule endoscope 10 is a capsule medical device that is introduced into a body cavity of a subject, and a permanent magnet is provided inside the capsule endoscope 10. The guiding device 20 generates a magnetic field MG and guides the capsule endoscope 10 introduced into a subject.

The capsule endoscope 10 is introduced into an organ of a subject together with a predetermined liquid by means of oral ingestion or the like, moves through the inside of a digestive tract, and is eventually discharged to the outside of the subject. During this time, the capsule endoscope 10 floats in the liquid introduced into the organ of the subject such as a stomach, and sequentially captures in-vivo images while being guided by the magnetic field MG. The capsule endoscope 10 then sequentially and wirelessly transmits image data corresponding to the in-vivo images obtained by the imaging.

Figure 2:
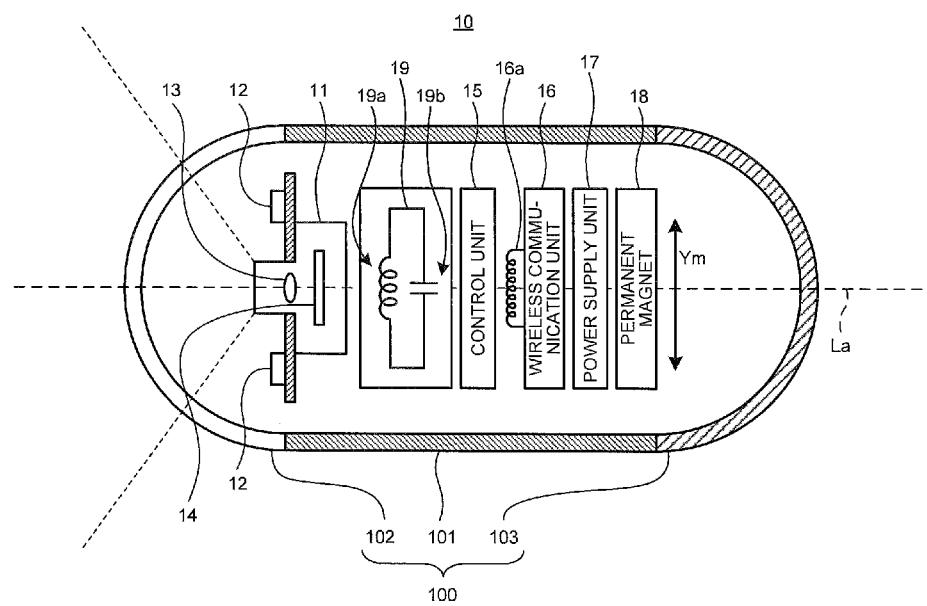
FIG. 2 is a schematic diagram illustrating an exemplary internal structure of a capsule endoscope illustrated in FIG. 1.

FIG. 2 is a schematic diagram illustrating an exemplary internal structure of the capsule endoscope 10. As illustrated in FIG. 2, the capsule endoscope 10 includes a capsule-shaped casing 100, an imaging unit 11, a control unit 15, a wireless communication unit 16, a power supply unit 17, a permanent magnet 18, and a position detecting magnetic field generation unit 19. The capsule-shaped casing 100 is an exterior formed to have such a size as to allow itself to be easily introduced into an organ of a subject. The imaging unit 11 outputs an image signal of the inside of a subject that has been captured. The control unit 15 processes the image signal output from the imaging unit 11 and controls each element of the capsule endoscope 10. The wireless communication unit 16 wirelessly transmits the image signal processed by the control unit 15 to the outside of the capsule endoscope 10. The power supply unit 17 supplies power to each element of the capsule endoscope 10. The permanent magnet 18 enables the guiding device 20 to perform guidance. The position detecting magnetic field generation unit 19 generates a position detecting magnetic field that is a magnetic field used for detecting a position of the capsule endoscope 10.

The capsule-shaped casing 100 is an outer casing formed to have such a size as to allow itself to be introduced into an organ of a subject. The capsule-shaped casing 100 has a tubular casing 101 and dome-shaped casings 102 and 103, and is configured such that both opening ends of the tubular casing 101 are closed by the dome-shaped casings 102 and 103. Each of the tubular casing 101 and the dome-shaped casing 103 is a colored casing that is substantially opaque to visible light. The dome-shaped casing 102 is a dome-like optical member that is transparent to light having a predetermined wavelength band such as visible light. As illustrated in FIG. 2, this capsule-shaped casing 100 liquid-tightly contains the imaging unit 11, the control unit 15, the wireless communication unit 16, the power supply unit 17, the permanent magnet 18, and the position detecting magnetic field generation unit 19.

The imaging unit 11 has an illumination unit 12 such as an LED, an optical system 13 such as a condenser lens, and an image sensor 14 such as a CMOS image sensor or a CCD. The illumination unit 12 emits illumination light such as white light to an imaging field of the image sensor 14 to irradiate a subject within the imaging field through the dome-shaped casing 102. The optical system 13 collects reflected light from the imaging field onto an imaging surface of the image sensor 14 to form an image. The image sensor 14 converts the reflected light from the imaging field received on the imaging surface, into an electrical signal, and outputs the electrical signal as an image signal.

The control unit 15 controls operation of the imaging unit 11 and operation of the wireless communication unit 16 and controls input and output of a signal between these elements. More specifically, the control unit 15 causes the image sensor 14 to capture a subject within the imaging field illuminated with the illumination unit 12, and performs a predetermined signal process on an image signal output from the image sensor 14. The control unit 15 further causes the wireless communication unit 16 to sequentially and wirelessly transmit the above-mentioned image signals subjected to the signal process in time series.

The wireless communication unit 16 obtains, from the control unit 15, an image signal of an in-vivo image output from the imaging unit 11, and performs a modulation process or the like on the image signal to generate a wireless signal. The wireless communication unit 16 includes an antenna 16a for transmitting a wireless signal, and wirelessly transmits the generated wireless signal via the antenna 16a.

The power supply unit 17 is a power storage unit such as a button type battery and a capacitor, and has a switch unit such as a magnetic switch or an optical switch. If the power supply unit 17 has the magnetic switch, the power supply unit 17 switches power supply on and off by a magnetic field applied from the outside. In the on state, power in the power storage unit is appropriately supplied to each element of the capsule endoscope 10, that is, the imaging unit 11, the control unit 15, and the wireless communication unit 16. In the off state, the power supply unit 17 stops supplying power to each element of the capsule endoscope 10.

The permanent magnet 18 enables the magnetic field MG to guide the capsule endoscope 10. The magnetic field MG is generated by a magnetic field generating unit 25 which will be described later. The permanent magnet 18 is arranged to be fixed within the capsule-shaped casing 100 so that a magnetization direction Ym is inclined to a long axis La. In the present embodiment, the permanent magnet 18 is arranged so that the magnetization direction Ym is orthogonal to the long axis La. The permanent magnet 18 operates in accordance with a magnetic field applied from the outside. As a result, guidance for the capsule endoscope 10 by the magnetic field generating unit 25 is realized.

The position detecting magnetic field generation unit 19 serves as a part of a resonance circuit and includes a marker coil 19a and a capacitor 19b. The marker coil 19a generates a magnetic field by means of current flow. The capacitor 19b forms the resonance circuit in cooperation with the marker coil 19a. The position detecting magnetic field generation unit 19 receives the power supply from the power supply unit 17 to generate a position detecting magnetic field having a predetermined frequency.

Referring again to FIG. 1, the guiding device 20 includes a receiving unit 21, a position and posture detecting unit 22, a display unit 23, an operation input unit 24, the magnetic field generating unit 25, a control unit 26, and a storage unit 27. The receiving unit 21 wirelessly communicates with the capsule endoscope 10 to receive a wireless signal including an image signal transmitted from the capsule endoscope 10. The position and posture detecting unit 22 detects a position and a posture of the capsule endoscope 10 within a subject based on a position detecting magnetic field generated by the position detecting magnetic field generation unit 19 of the capsule endoscope 10. The display unit 23 obtains an image signal from the wireless signal received by the receiving unit 21, performs a predetermined signal process on the image signal to display an in-vivo image, and displays information such as the position and the posture of the capsule endoscope 10 within the subject. The operation input unit 24 accepts input of information or the like including an instruction for various types of operation in the capsule medical device guiding system 1. The magnetic field generating unit 25 generates a magnetic field for guiding the capsule endoscope 10. The control unit 26 controls each of these elements. The storage unit 27 stores image data or the like of an in-vivo image.

Figure 3:
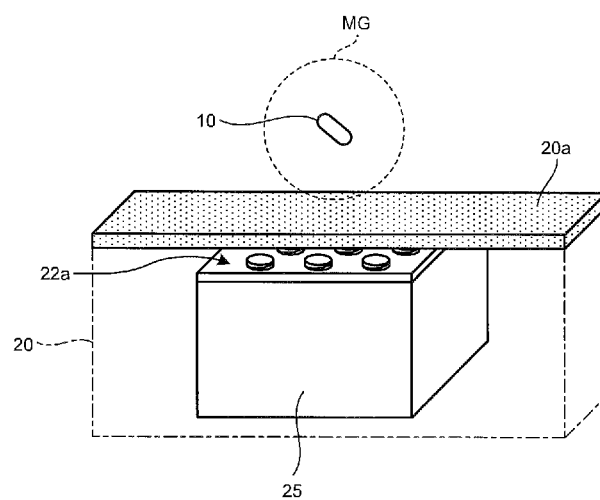
FIG. 3 is a schematic diagram illustrating an exemplary configuration of an external appearance of a guiding device illustrated in FIG. 1.

FIG. 3 is a perspective diagram schematically illustrating an external appearance of the guiding device 20. As illustrated in FIG. 3, the guiding device 20 is provided with a bed 20a as a table on which a subject is placed. Below the bed 20a, at least the magnetic field generating unit 25 and a plurality of sensing coils 22a are arranged. The magnetic field generating unit 25 generates the magnetic field MG. The plurality of sensing coils 22a detects a position detecting magnetic field generated by the position detecting magnetic field generation unit 19.

The receiving unit 21 includes a plurality of receiving antennas 21a and sequentially receives wireless signals from the capsule endoscope 10 via these receiving antennas 21a. The receiving unit 21 selects an antenna having the highest reception electric field strength from among these receiving antennas 21a, and performs a demodulation process or the like on a wireless signal from the capsule endoscope 10 received via the selected antenna. The receiving unit 21 thus extracts an image signal from the wireless signal and outputs the image signal to the display unit 23.

The plurality of sensing coils 22a is arranged on a planar panel arranged in parallel with an upper surface of the bed 20a. Each of the sensing coils 22a, for example, is a cylindrical coil formed in a coil spring shape, and receives a magnetic field generated by the position detecting magnetic field generation unit 19 of the capsule endoscope 10 to output a detection signal.

The position and posture detecting unit 22 obtains a plurality of detection signals output from the respective plurality of sensing coils 22a, and performs, on these detection signals, signal processes such as waveform shaping, amplification, A/D conversion, and FFT. The position and posture detecting unit 22 thus extracts magnetic field information such as amplitude and a phase of a position detecting magnetic field. The position and posture detecting unit 22 further calculates the position and the posture of the capsule endoscope 10 based on this magnetic field information, and outputs the position and the posture of the capsule endoscope 10 as positional information.

A method for detecting the position and the posture of the capsule endoscope 10 is not limited to the above-mentioned method using the position detecting magnetic field. For example, the position and the posture of the capsule endoscope 10 may be detected based on strength distribution of a wireless signal received by the receiving unit 21. For instance, as disclosed in JP 2007-283001 A, the position of the capsule endoscope 10 can be obtained in such a manner that an initial value of the position of the capsule endoscope 10 is appropriately set, and a process of calculating an estimate value of the position by means of the Gauss-Newton method is repeated until a shift amount between the calculated estimate value and a previous estimate value becomes equal to or less than a predetermined value.

The display unit 23 has a screen including various displays such as a liquid crystal display. The display unit 23 displays, on the screen, an in-vivo image that is based on an image signal input from the receiving unit 21, positional information of the capsule endoscope 10, and various other types of information.

The operation input unit 24 inputs operation input information into the control unit 26 in accordance with external operation by a user. The operation input information is instruction information for controlling the position or the posture of the capsule endoscope 10. The operation input unit 24 includes, for example, a joystick, a console including various buttons and various switches, and an input device such as a keyboard.

The operation input information specifically includes information about translation operation, tilt angle changing operation, and azimuth angle changing operation or the like. The translation operation translates the capsule endoscope 10 in a horizontal direction or a vertical direction. The tilt angle changing operation changes a tilt angle of the long axis La of the capsule endoscope 10 with respect to the vertical direction. The azimuth angle changing operation changes an azimuth angle of the field of the imaging unit 11 provided in the capsule endoscope 10, that is, an angle around an axis in the vertical direction.

The magnetic field generating unit 25 generates the magnetic field MG for changing, relative to a subject, the position, the tilt angle, and the azimuth angle of the capsule endoscope 10 introduced into the subject. The magnetic field generating unit 25 has an extracorporeal permanent magnet 25a, an in-plane position changing unit 25b, a vertical position changing unit 25c, an elevation angle changing unit 25d, and a turning angle changing unit 25e. The extracorporeal permanent magnet 25a generates the magnetic field MG. The in-plane position changing unit 25b, the vertical position changing unit 25c, the elevation angle changing unit 25d, and the turning angle changing unit 25e change the position and the posture of the extracorporeal permanent magnet 25a.

Figure 4:
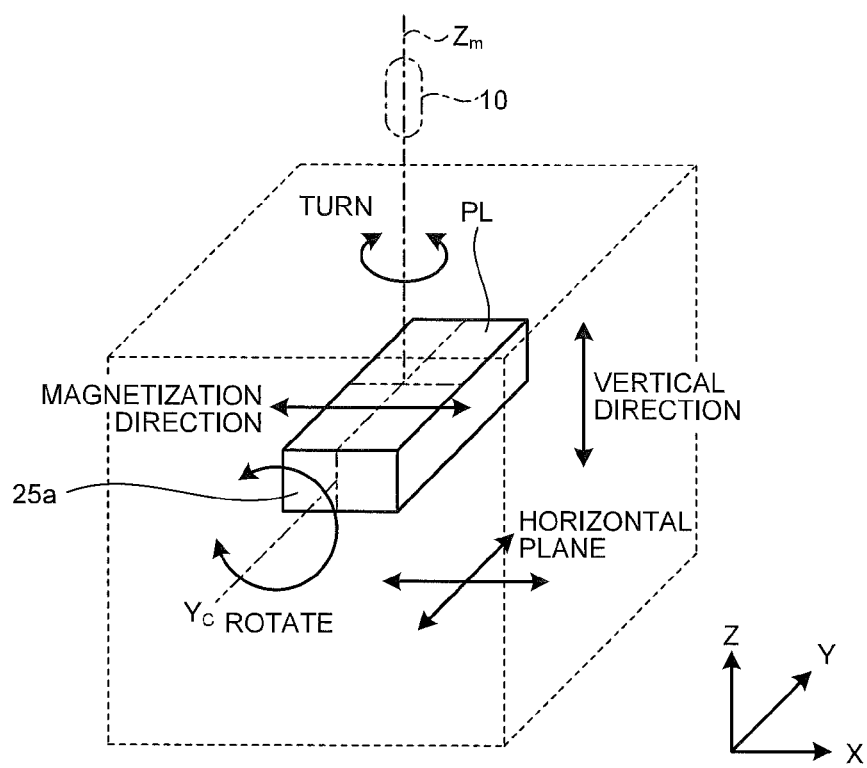
FIG. 4 is a schematic diagram for explaining an installation state of an extracorporeal permanent magnet illustrated in FIG. 1.

FIG. 4 is a schematic diagram for explaining an installation state of the extracorporeal permanent magnet 25a. As illustrated in FIG. 4, for example, the extracorporeal permanent magnet 25a includes a bar magnet having a rectangular parallelepiped shape. In an initial state, the extracorporeal permanent magnet 25a is arranged so that one of four surfaces parallel to a magnetization direction of the extracorporeal permanent magnet 25a is parallel to a horizontal plane (XY plane) that is a plane orthogonal to a gravity direction. Hereinafter, the arrangement of the extracorporeal permanent magnet 25a in the initial state of the extracorporeal permanent magnet 25a is referred to as reference arrangement. One of the four surfaces parallel to the magnetization direction of the extracorporeal permanent magnet 25a which faces the capsule endoscope 10 is also referred to as a capsule facing surface PL.

The in-plane position changing unit 25b translates the extracorporeal permanent magnet 25a on the horizontal plane. Specifically, the extracorporeal permanent magnet 25a moves on the horizontal plane while a relative position between two magnetic poles magnetized in the extracorporeal permanent magnet 25a is secured.

The vertical position changing unit 25c is a translation mechanism that translates the extracorporeal permanent magnet 25a along the vertical direction (Z direction). Specifically, the extracorporeal permanent magnet 25a moves along the vertical direction while the relative position between the two magnetic poles magnetized in the extracorporeal permanent magnet 25a is secured.

The elevation angle changing unit 25d is a rotation mechanism that rotates the extracorporeal permanent magnet 25a on a vertical plane including the magnetization direction of the extracorporeal permanent magnet 25a to change an angle of the magnetization direction with respect to the horizontal plane. In other words, the elevation angle changing unit 25d rotates the extracorporeal permanent magnet 25a around an axis $Y_C$ in a Y direction. The axis $Y_C$ is parallel to the capsule facing surface PL, orthogonal to the magnetization direction, and passes through the center of the extracorporeal permanent magnet 25a. Hereinafter, an angle between the extracorporeal permanent magnet 25a and the horizontal plane is referred to as an elevation angle.

The turning angle changing unit 25e rotates the extracorporeal permanent magnet 25a around a vertical axis $Z_m$ passing through the center of the extracorporeal permanent magnet 25a. Hereinafter, a rotational motion of the extracorporeal permanent magnet 25a around the vertical axis $Z_m$ is referred to as a turning motion. An angle of the turned extracorporeal permanent magnet 25a with respect to the reference arrangement is referred to as a turning angle.

The control unit 26 controls operation of each element of the magnetic field generating unit 25 based on positional information of the capsule endoscope 10 input from the position and posture detecting unit 22 and operation input information input from the operation input unit 24. The control unit 26 thus changes a relative position between the extracorporeal permanent magnet 25a and a subject, a distance between the extracorporeal permanent magnet 25a and the capsule endoscope 10, and a rotation angle of the extracorporeal permanent magnet 25a from the reference arrangement, namely, the elevation angle and the turning angle, whereby the capsule endoscope 10 is guided. A control mode that is executed by the control unit 26 includes a first control mode and a second control mode. In the first control mode, the capsule endoscope 10 is moved to an appropriate position relative to distribution of the magnetic field MG generated by the extracorporeal permanent magnet 25a based on positional information. In the second control mode, feedback control is performed based on positional information in accordance with operation input information, whereby the capsule endoscope 10 is guided to a position and a posture desired by a user.

The storage unit 27 includes a storage medium and a writing reading device. The storage medium, such as a flash memory or a hard disk, saves information in a rewritable manner. The writing reading device writes and reads information to and from the storage medium. The storage unit 27 stores image data of an in-vivo image group of a subject captured by the capsule endoscope 10. The storage unit 27 also stores information such as various programs and various parameters that is used by the control unit 26 to control each element of the guiding device 20.

Figure 5:
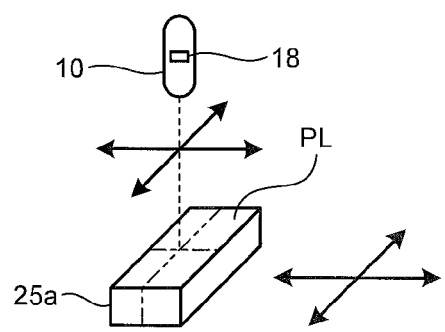
FIG. 5 is a schematic diagram for explaining a guiding method for translating the capsule endoscope on a horizontal plane.

Next, reference will be made to a guiding method for the position and the posture of the capsule endoscope 10 performed by a magnetic field generated by the magnetic field generating unit 25. FIG. 5 is a schematic diagram for explaining a guiding method for translating the capsule endoscope 10 on the horizontal plane. When the capsule endoscope 10 is translated on the horizontal plane, a magnetic field is generated to create magnetic attractive force in such a direction as to restrain the capsule endoscope 10 at a specific position on the horizontal plane, and the magnetic field is applied to the permanent magnet 18 of the capsule endoscope 10. This specific position is hereinafter referred to as a restrained position. As illustrated in FIG. 5, the permanent magnet 18 is attracted to the restrained position and the capsule endoscope 10 is thus restrained. In this state, the extracorporeal permanent magnet 25a is moved on the horizontal plane by the in-plane position changing unit 25b, whereby the capsule endoscope 10 is translated on the horizontal plane.

Figure 6:
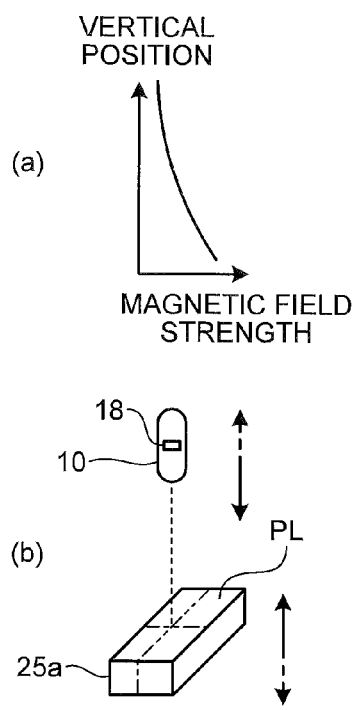
FIG. 6 is a schematic diagram for explaining a guiding method for translating the capsule endoscope in a vertical direction.

FIG. 6 is a schematic diagram for explaining a guiding method for translating the capsule endoscope 10 in the vertical direction. When the capsule endoscope 10 is translated in the vertical direction, as illustrated in (a) of FIG. 6, such a magnetic field that distribution of a magnetic force gradient varies depending on a distance in a direction orthogonal to the capsule facing surface PL is applied to the permanent magnet 18 of the capsule endoscope 10. More specifically, the extracorporeal permanent magnet 25a is moved in the vertical direction by the vertical position changing unit 25c, and a distance between the extracorporeal permanent magnet 25a and the permanent magnet 18 is changed. Consequently, as illustrated in (b) of FIG. 6, the capsule endoscope 10 is translated in the vertical direction.

In distribution of a magnetic field generated by the extracorporeal permanent magnet 25a formed in a rectangular parallelepiped shape as illustrated in FIG. 4, the restrained position of the capsule endoscope 10 is located on a line orthogonal to the capsule facing surface PL and passing through the center of the extracorporeal permanent magnet 25a.

Figure 7:
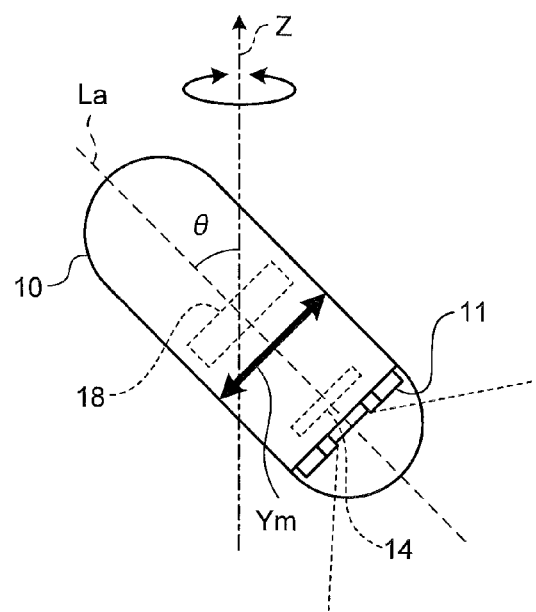
FIG. 7 is a schematic diagram for explaining a guiding method for changing a tilt angle and an azimuth angle of the capsule endoscope.

FIG. 7 is a schematic diagram for explaining a guiding method for changing the tilt angle and the azimuth angle of the capsule endoscope 10. When a tilt angle θ of the long axis La of the capsule endoscope 10 with respect to the vertical direction is changed, the capsule endoscope 10 is restrained at the restrained position, and the extracorporeal permanent magnet 25a is rotated around the axis $Y_C$ by the elevation angle changing unit 25d, whereby the elevation angle is changed. As a result, the tilt angle θ of the capsule endoscope 10 is changed. When the azimuth angle of the capsule endoscope 10 is changed, the capsule endoscope 10 is restrained at the restrained position, and the extracorporeal permanent magnet 25a is rotated around the vertical axis $Z_m$ passing through the center of the extracorporeal permanent magnet 25a by the turning angle changing unit 25e, whereby the turning angle is changed. As a result, the capsule endoscope 10 is rotated around a Z axis, and the azimuth angle of the capsule endoscope 10 is changed. At this time, when the elevation angle changing unit 25d and the turning angle changing unit 25e rotate the extracorporeal permanent magnet 25a, the restrained position is moved with respect to the extracorporeal permanent magnet 25a. In this regard, the control unit 26 calculates the restrained position based on the elevation angle and the turning angle of the extracorporeal permanent magnet 25a, a distance between the extracorporeal permanent magnet 25a and the horizontal plane including the position of the capsule endoscope 10, a magnetic property of the capsule endoscope 10 such as a magnetic moment, and a geometric property of the capsule endoscope 10 such as volume, mass, and a centroid position. Then, the in-plane position changing unit 25b is controlled in accordance with the elevation angle and the turning angle of the extracorporeal permanent magnet 25a so that the restrained position is not moved.

Figure 8:
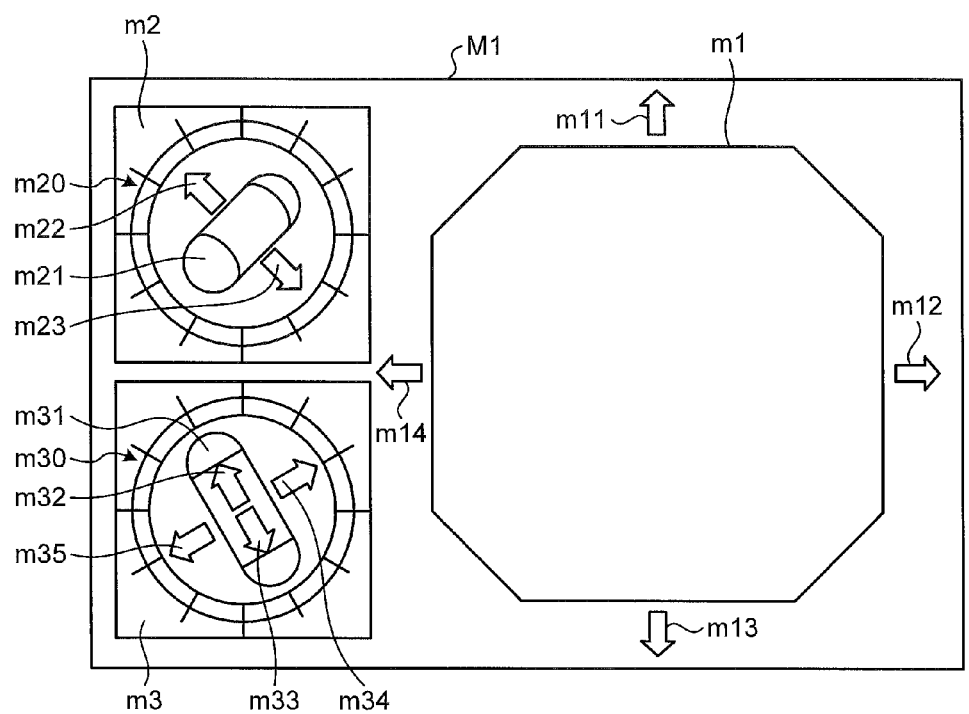
FIG. 8 is a diagram illustrating an exemplary screen displayed on a display unit illustrated in FIG. 1.

FIG. 8 is a schematic diagram illustrating an exemplary screen displayed on the display unit 23. A screen M1 illustrated in FIG. 8 includes an image display area m1 and posture diagrams m2, m3. On the image display area m1, an in-vivo image obtained by the capsule endoscope 10 is displayed. The posture diagrams m2, m3 indicate the posture of the capsule endoscope 10 within a subject. In the present embodiment, as illustrated in the image display area m1, four corners of a rectangular in-vivo image are masked and displayed.

The image display area m1 is an area on which an in-vivo image is displayed based on image signals sequentially input from the receiving unit 21. Operation input arrows m11 to m14 are displayed around the image display area m1. Each of the operation input arrows m11 to m14 serves as a sign indicating a direction of operation input for translating the capsule endoscope 10.

The posture diagram m2 represents the posture of the capsule endoscope 10 on the horizontal plane and includes a scale m20, a model diagram m21, and operation input arrows m22, m23. The scale m20 indicates the azimuth angle. The model diagram m21 represents the posture of the capsule endoscope 10. Each of the operation input arrows m22, m23 serves as a sign indicating a direction of operation input for turning the capsule endoscope 10.

The posture diagram m3 represents the posture of the capsule endoscope 10 on the vertical plane and includes a scale m30, a model diagram m31, operation input arrows m32, m33, and operation input arrows m34, m35. The scale m30 indicates the tilt angle. The model diagram m31 represents the posture of the capsule endoscope 10. Each of the operation input arrows m32, m33 serves as a sign indicating a direction in which operation input for translating the capsule endoscope 10 in a long axis direction is performed. Each of the operation input arrows m34, m35 serves as a sign indicating a direction of operation input for tilting the capsule endoscope 10.

The operation input arrows m11 to m14, m22, m23, and m32 to m35 are set so as to be displayed in different forms in accordance with the control mode being executed by the control unit 26 and whether the capsule endoscope 10 can be guided. In the present embodiment, colors of the operation input arrows m11 to m14, m22, m23, and m32 to m35 are changed. For example, during a wait for operation input for the capsule endoscope 10, the operation input arrows m11 to m14, m22, m23, and m32 to m35 are displayed in white. When operation input is performed while the capsule endoscope 10 can be appropriately guided, the operation input arrow of a direction in which the operation input has been performed is displayed in light blue. When operation input is performed while the capsule endoscope 10 is difficult to guide appropriately, the operation input arrow of a direction in which the operation input has been performed is displayed in yellow. When no operation input for the capsule endoscope 10 is allowed, the operation input arrows m11 to m14, m22, m23, and m32 to m35 are set to be not displayed.

Operation input information input from the operation input unit 24 is reflected in a control signal that is output when the control unit 26 controls the magnetic field generating unit 25. Therefore, the postures of the model diagrams m21, m31 of the capsule endoscope 10 displayed on the posture diagrams m2, m3 can be considered to be substantially the same as the posture of the actual capsule endoscope 10 in a subject.

Figure 9:
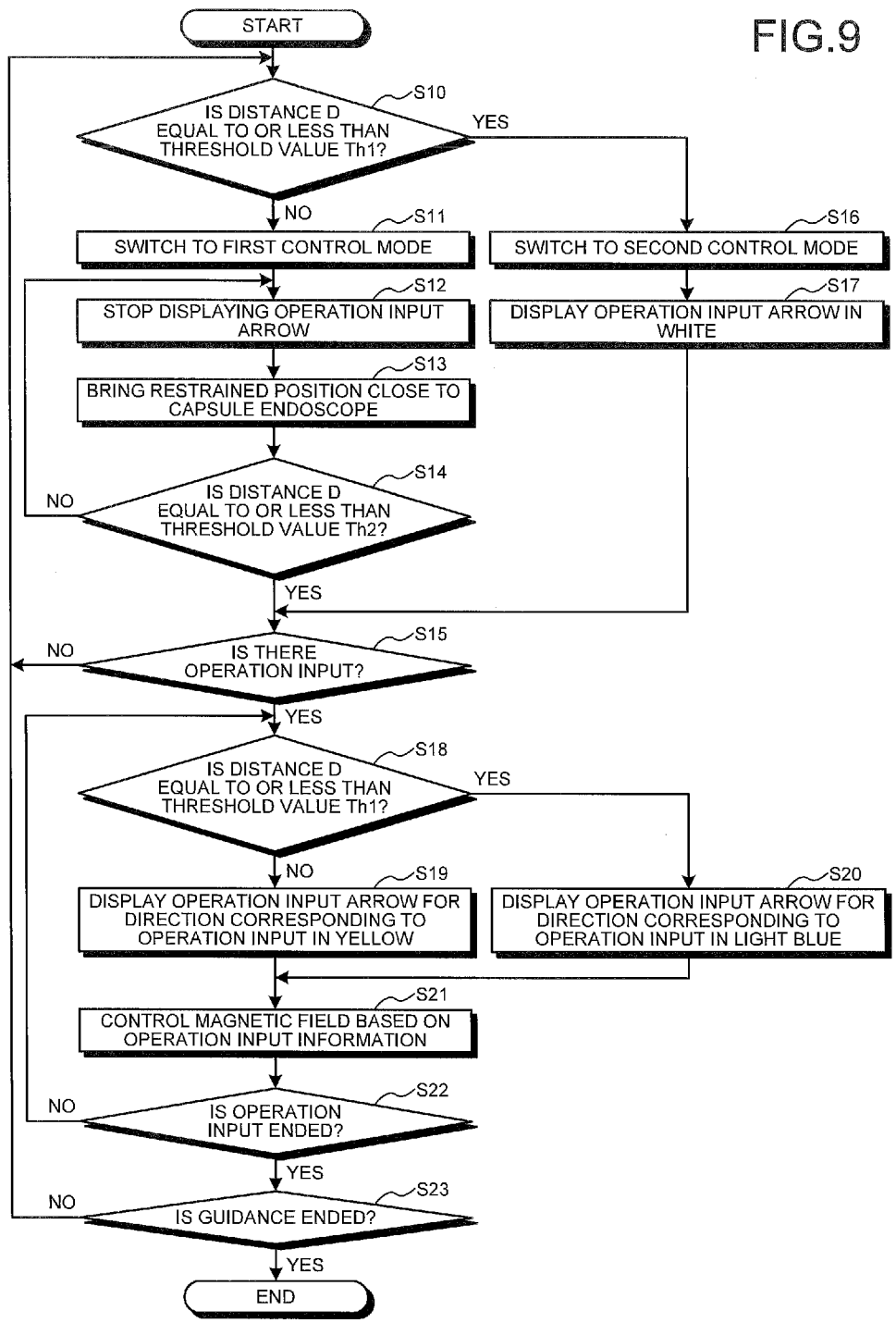
FIG. 9 is a flowchart illustrating operation of the capsule medical device guiding system illustrated in FIG. 1.
Figure 10:
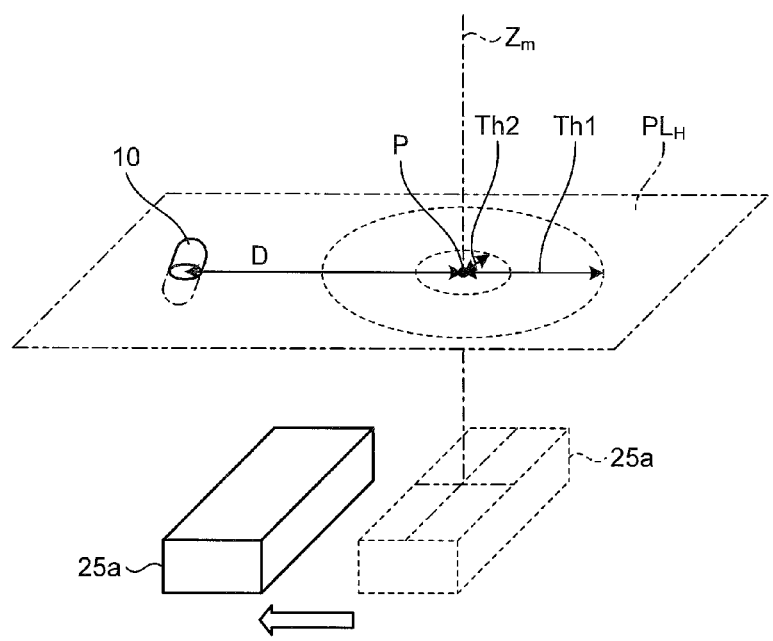
FIG. 10 is a schematic diagram for explaining a guiding method for the capsule endoscope in the capsule medical device guiding system illustrated in FIG. 1.
Figure 11:
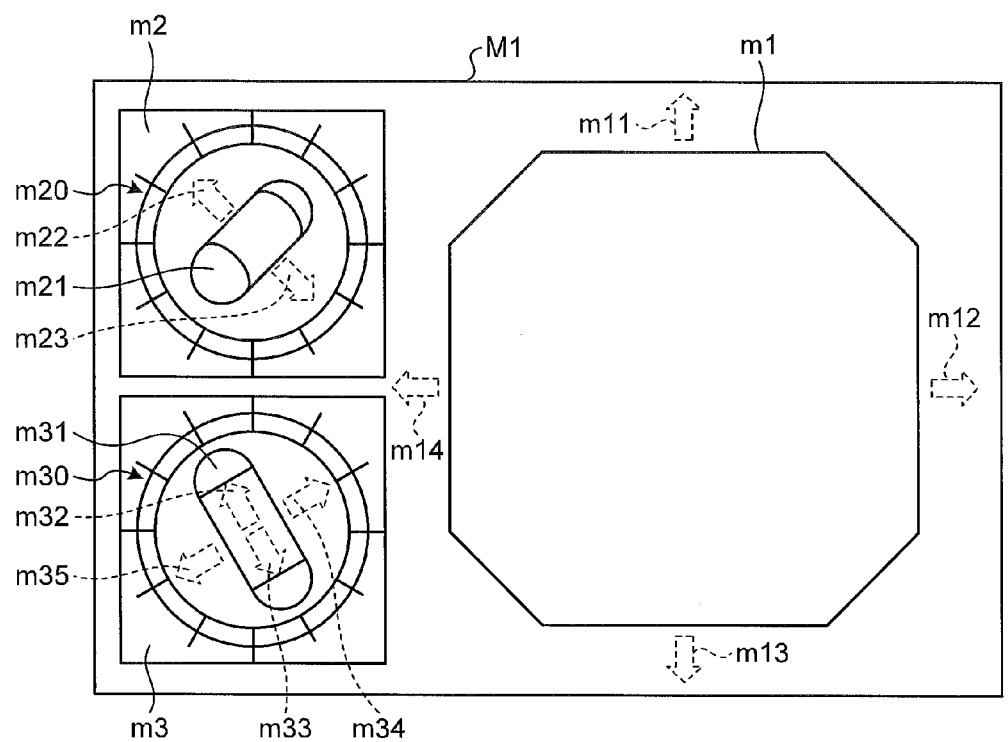
FIG. 11 is a schematic diagram illustrating an exemplary screen displayed on the display unit during the operation of the capsule medical device guiding system illustrated in FIG. 1.
Figure 12:
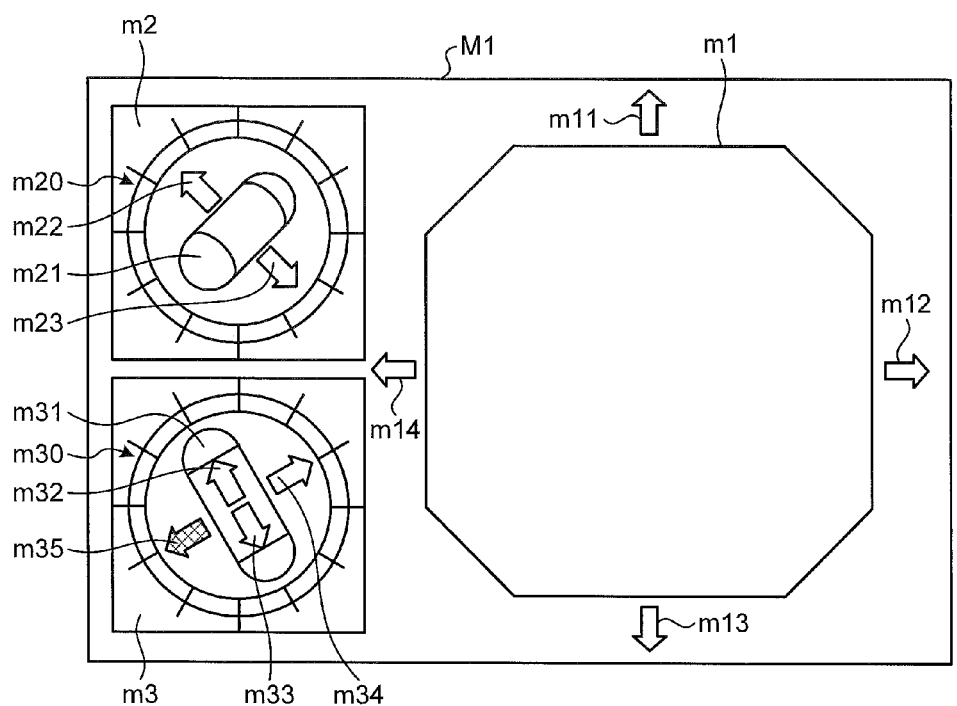
FIG. 12 is a schematic diagram illustrating an exemplary screen displayed on the display unit during the operation of the capsule medical device guiding system illustrated in FIG. 1.

Next, operation of the capsule medical device guiding system (hereinafter simply referred to as a system) 1 will be described. FIG. 9 is a flowchart illustrating the operation of the system 1. FIG. 10 is a schematic diagram for explaining a guiding method for the capsule endoscope 10 in the system 1. In FIG. 10, the extracorporeal permanent magnet 25a and a movement on an arbitrary horizontal plane $PL_H$ of the capsule endoscope 10 guided by a magnetic field generated by the extracorporeal permanent magnet 25a are illustrated. FIGS. 11 and 12 are schematic diagrams illustrating exemplary screens displayed on the display unit 23 during the operation of the system 1.

When the system 1 starts guiding the capsule endoscope 10, first, in step S10, the control unit 26 determines whether a distance D between a restrained position P in the magnetic field generated by the magnetic field generating unit 25 and a current position of the capsule endoscope 10 on the horizontal plane $PL_H$ including the position of the capsule endoscope 10 is equal to or less than a first threshold value Th1 based on positional information output from the position and posture detecting unit 22. The restrained position P in the magnetic field generated by the magnetic field generating unit 25 is calculated based on the elevation angle and the turning angle of the extracorporeal permanent magnet 25a, the distance between the extracorporeal permanent magnet 25a and the horizontal plane $PL_H$ including the position of the capsule endoscope 10, the magnetic property of the capsule endoscope 10, namely, the magnetic moment, and the geometric property of the capsule endoscope 10, namely, the volume, the mass, and the centroid position. The threshold value Th1 is set in advance as a limit distance of a range in which the capsule endoscope 10 can be guided by the magnetic field generated by the magnetic field generating unit 25.

When the distance D is greater than the threshold value Th1 (step S10: No), the control unit 26 switches to the first control mode (step S11).

In the subsequent step S12, as illustrated in FIG. 11, the display unit 23 stops displaying all the operation input arrows m11 to m14, m22, m23, and m32 to m35 on the screen M1 under the control of the control unit 26. This allows a user to recognize that acceptance of operation input for guiding the capsule endoscope 10 is under suspension.

In the subsequent step S13, the magnetic field generating unit 25 changes the distribution of the magnetic field such that the restrained position P is brought close to the capsule endoscope 10 under the control of the control unit 26. More specifically, as illustrated in FIG. 10, the extracorporeal permanent magnet 25a is translated on the horizontal plane $PL_H$ so that the vertical axis $Z_m$ is brought close to the capsule endoscope 10.

In the subsequent step S14, the control unit 26 determines whether the distance D is equal to or less than a second threshold value Th2 based on positional information output from the position and posture detecting unit 22. The threshold value Th2 is set to a value less than the threshold value Th1 in advance as a limit distance by which the capsule endoscope 10 can be appropriately guided by the magnetic field generated by the magnetic field generating unit 25.

When the distance D is greater than the threshold value Th2 (step S14: No), the operation of the system 1 proceeds to step S12.

On the other hand, when the distance D is equal to or less than the threshold value Th2 (step S14: Yes), the control unit 26 determines whether operation input for the operation input unit 24 for guiding the position or the posture of the capsule endoscope 10 is performed (step S15).

When the operation input for the operation input unit 24 for guiding the position or the posture of the capsule endoscope 10 is not performed (step S15: No), the operation of the system 1 proceeds to step S10.

In step S10, when the distance D is equal to or less than the threshold value Th1 (step S10: Yes), the control unit 26 switches to the second control mode (step S16).

In the subsequent step S17, as illustrated in FIG. 8, the display unit 23 displays all the operation input arrows m11 to m14, m22, m23, and m32 to m35 on the screen M1 in white under the control of the control unit 26. This allows the user to recognize that the operation input for the operation input unit 24 for guiding the capsule endoscope 10 is enabled. After that, the operation of the system 1 proceeds to step S15.

In step S15, when the operation input for the operation input unit 24 for guiding the position or the posture of the capsule endoscope 10 is performed (step S15: Yes), the control unit 26 determines whether the distance D is equal to or less than the threshold value Th1 (step S18).

When the distance D is greater than the threshold value Th1 (step S18: No), as illustrated in FIG. 12, the display unit 23 displays, under the control of the control unit 26, the operation input arrow for a direction corresponding to the operation input, e.g., the operation input arrow m35, in yellow, for example (step S19). In FIG. 12, a difference in color is indicated by a difference in pattern. This allows the user to recognize a possibility that the guidance for the capsule endoscope 10 intended by the user is not realized since the capsule endoscope 10 has gone out of the range in which the capsule endoscope 10 can be guided by the magnetic field.

The color indicating the operation input arrow for the direction corresponding to the operation input is not limited to yellow as long as the color is different from that of the operation input arrow of another direction. It is preferable to display a conspicuous color so that the user can be alerted that the distance D is greater than the threshold value Th1. After that, the operation of the system 1 proceeds to step S21.

On the other hand, when the distance D is equal to or less than the threshold value Th1 (step S18: Yes), the display unit 23 displays, under the control of the control unit 26, the operation input arrow for a direction corresponding to the operation input, in light blue, for example (step S20). This allows the user to confirm that the guidance for the capsule endoscope 10 is realized generally as intended by the user. In step S20, the color indicating the operation input arrow for the direction corresponding to the operation input is not limited to light blue as long as the color is different from that of the operation input arrow for another direction, i.e., different from white, and the color is different from that of the operation input arrow of the direction in which the operation input is performed in step S19, i.e., different from yellow.

In the subsequent step S21, the magnetic field generating unit 25 controls the magnetic field based on operation input information input from the operation input unit 24 under the control of the control unit 26. As a result, the magnetic field for controlling the position or the posture of the capsule endoscope 10 is generated in a subject.

In the subsequent step S22, the control unit 26 determines whether operation input performed on the operation input unit 24 is ended. When the operation input is not ended (step S22: No), the operation of the system 1 returns to step S18.

On the other hand, when the operation input is ended (step S22: Yes), the control unit 26 determines whether an instruction to end the guidance for the capsule endoscope 10 is input (step S23). The instruction to end the guidance is input in accordance with predetermined operation for the operation input unit 24. When the guidance is not ended (step S23: No), the operation of the system 1 returns to step S10. On the other hand, when the guidance is ended (step S23: Yes), the operation of the system 1 is ended.

As described above, according to the embodiment of the present invention, when the distance between the restrained position P in the magnetic field generated by the magnetic field generating unit 25 and the capsule endoscope 10 becomes greater than the threshold value Th1 set as the range in which the capsule endoscope 10 can be guided by the magnetic field, the distribution of the magnetic field is changed and the restrained position P is automatically brought close to the capsule endoscope 10. Therefore, the guidance for the capsule endoscope 10 can be appropriately performed again.

In addition, according to the embodiment of the present invention, the color of the operation input arrow is changed and displayed in accordance with a situation, such as when the capsule endoscope 10 exists in the range in which the capsule endoscope 10 can be guided by the magnetic field, or when the capsule endoscope 10 goes out of this range. Therefore, the user can easily grasp whether the capsule endoscope 10 can be guided as intended by the user.

First Modification

Figure 13:
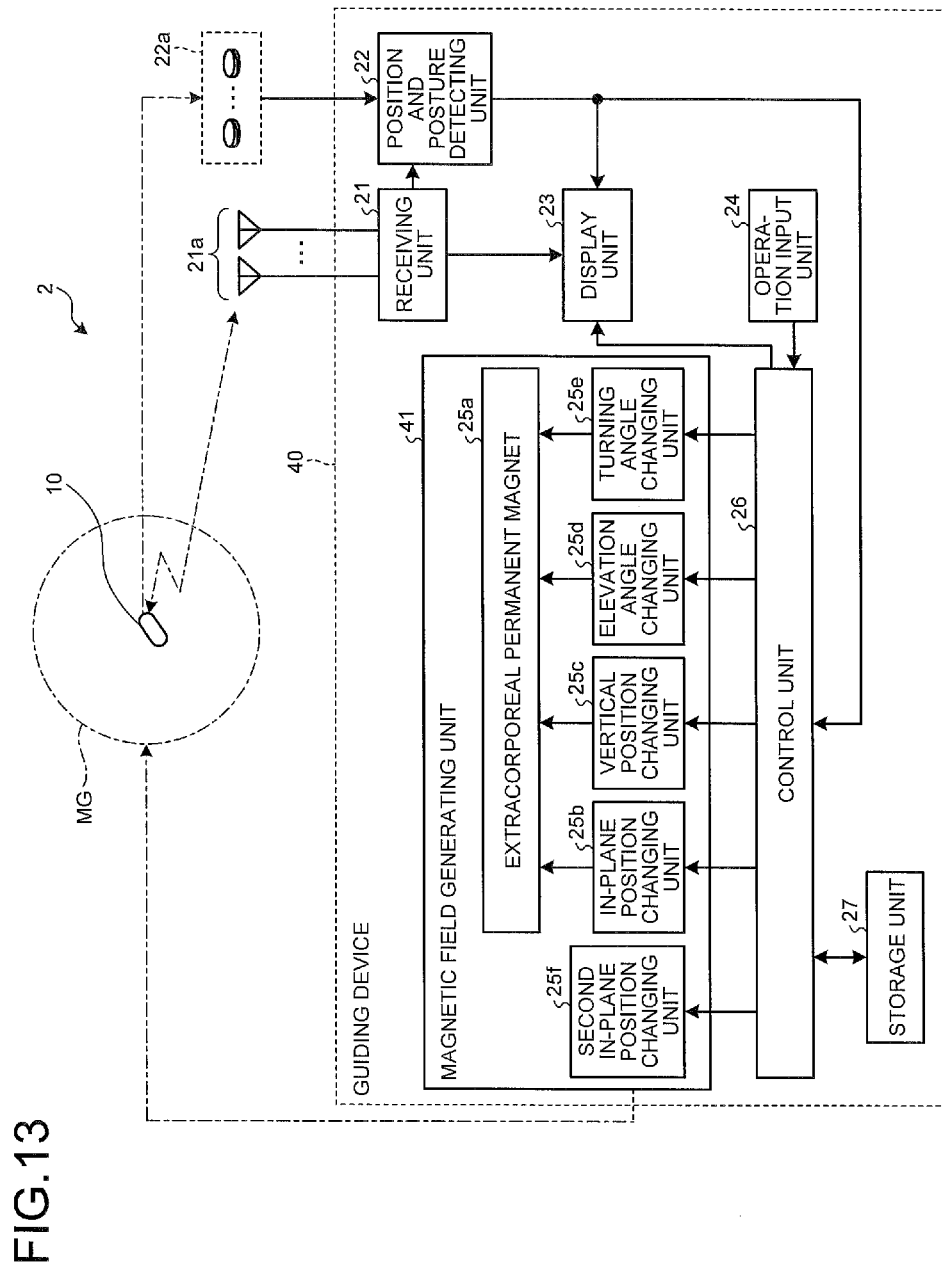
FIG. 13 is a diagram illustrating an exemplary configuration of a capsule medical device guiding system according to a first modification of the embodiment of the present invention.

Next, a first modification of the embodiment of the present invention will be described. FIG. 13 is a diagram illustrating an exemplary configuration of a capsule medical device guiding system according to the first modification of the embodiment of the present invention.

As illustrated in FIG. 13, a capsule medical device guiding system 2 according to the first modification includes a guiding device 40 having a magnetic field generating unit 41 in place of the guiding device 20 illustrated in FIG. 1. The magnetic field generating unit 41 further includes a second in-plane position changing unit 25f as compared with the magnetic field generating unit 25 illustrated in FIG. 1. A configuration of each element other than the second in-plane position changing unit 25f in the capsule medical device guiding system 2 is similar to that of the above-mentioned embodiment.

Figure 14:
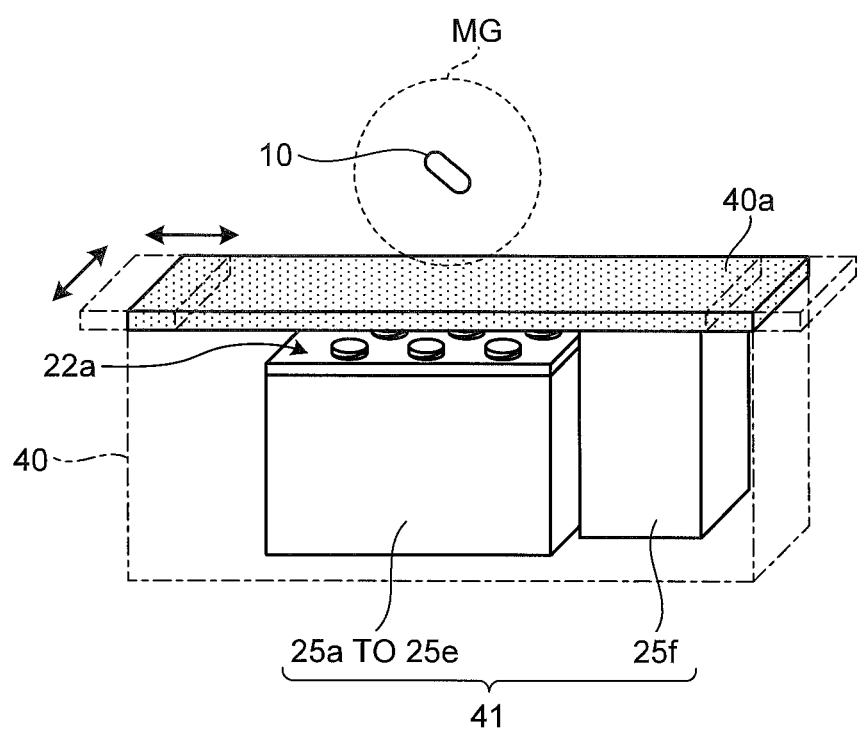
FIG. 14 is a schematic diagram illustrating an exemplary configuration of an external appearance of a guiding device illustrated in FIG. 13.

FIG. 14 is a schematic diagram illustrating an exemplary configuration of an external appearance of the guiding device 40 illustrated in FIG. 13. As illustrated in FIG. 14, the guiding device 40 is provided with a bed 40a as a table on which a subject is placed. The bed 40a can be translated in the horizontal direction. Below the bed 40a, the magnetic field generating unit 41 that generates the magnetic field MG is arranged.

The second in-plane position changing unit 25f is a translation mechanism that translates the bed 40a in the horizontal direction. The second in-plane position changing unit 25f moves the bed 40a with a subject placed thereon, whereby a relative position of the capsule endoscope 10 to the magnetic field MG generated by the extracorporeal permanent magnet 25a is changed.

In the capsule medical device guiding system 2 in the first modification, the bed 40a is moved in step S13 illustrated in FIG. 9, whereby the capsule endoscope 10 itself is brought close to the restrained position P. Alternatively, both the extracorporeal permanent magnet 25a and the bed 40a may be relatively moved to bring the capsule endoscope 10 and the restrained position P close to each other.

According to the first modification, even when the capsule endoscope 10 goes out of the range designated by the threshold value Th1, a distance for moving the extracorporeal permanent magnet 25a can be shortened.

Second Modification

Figure 15:
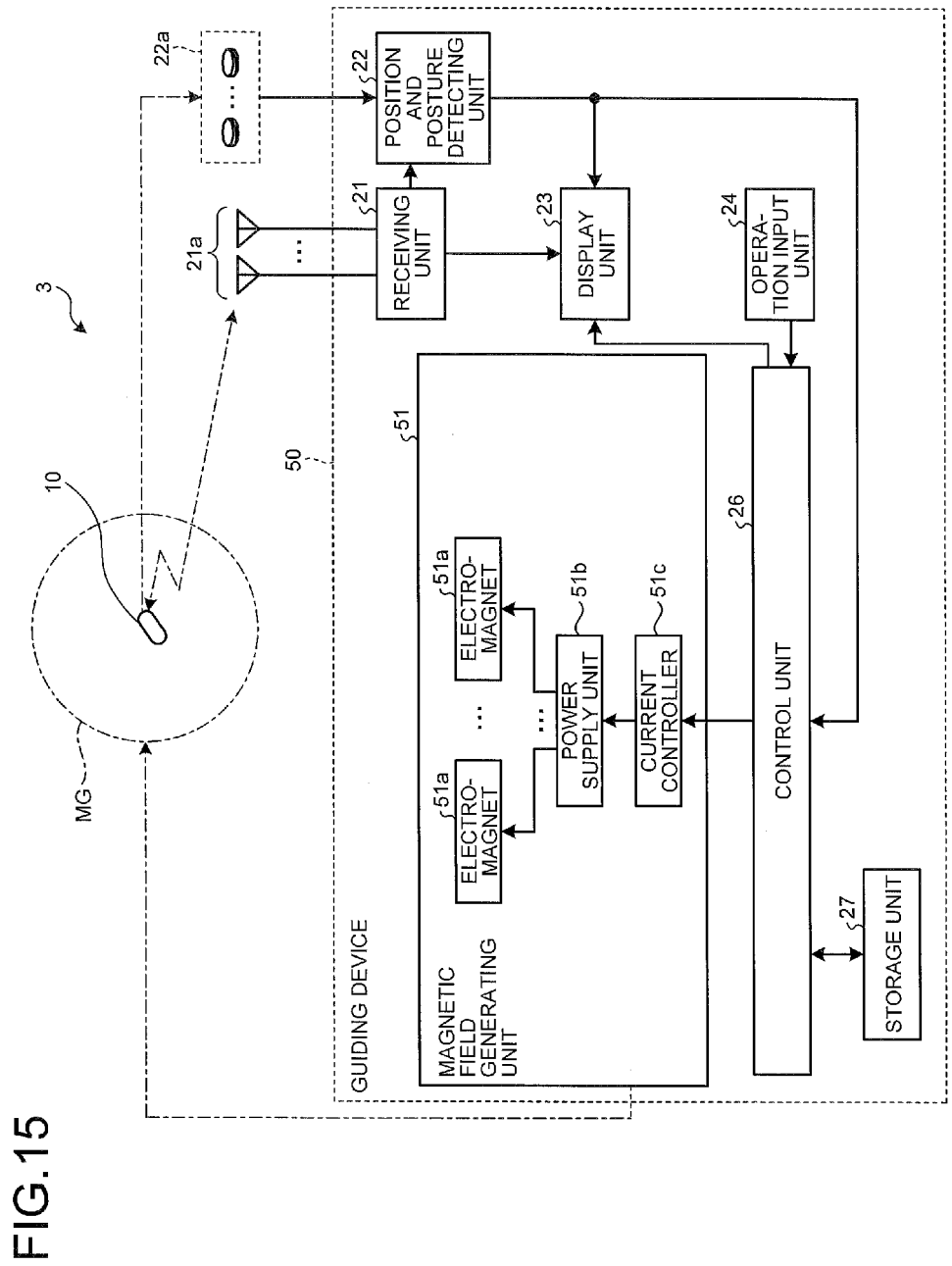
FIG. 15 is a diagram illustrating an exemplary configuration of a capsule medical device guiding system according to a second modification of the embodiment of the present invention.

Next, a second modification of the embodiment of the present invention will be described. FIG. 15 is a diagram illustrating an exemplary configuration of a capsule medical device guiding system according to the second modification of the embodiment of the present invention. As illustrated in FIG. 15, a capsule medical device guiding system 3 according to the second modification of the embodiment includes a guiding device 50 having a magnetic field generating unit 51 in place of the guiding device 20 illustrated in FIG. 1.

The magnetic field generating unit 51 includes a plurality of electromagnets 51a, a power supply unit 51b, and a current controller 51c. The power supply unit 51b supplies power to each of the electromagnets 51a. The current controller 51c controls current that flows into each of the electromagnets 51a under the control of the control unit 26. The current controller 51c controls the magnitude of the current that is supplied to each of the electromagnets 51a, whereby a synthetic magnetic field is generated to define a restrained position. The synthetic magnetic field is applied to the permanent magnet 18 within the capsule endoscope 10. A configuration of each element other than the magnetic field generating unit 51 in the capsule medical device guiding system 3 is similar to that of the above-mentioned embodiment.

In the capsule medical device guiding system 3 according to the second modification, current that is supplied to each of the electromagnets 51a is changed in step S13 illustrated in FIG. 9, and distribution of the synthetic magnetic field formed by these electromagnets 51a is changed, whereby the restrained position P is brought close to the capsule endoscope 10 as illustrated in FIG. 10.

According to the second modification, the distribution of the magnetic field to be applied to the capsule endoscope 10 can be changed without providing a mechanical movement mechanism or the like. Therefore, a quick response can be realized.

According to some embodiments, since distribution of a magnetic field relative to a capsule medical device is changed when a distance between a specific position, which is an original restrained position of the capsule medical device in the magnetic field generated by a magnetic field generating unit, and a current position of the capsule medical device becomes greater than a threshold value, it is possible to guide the capsule medical device without leaving the capsule medical device located off the restrained position.

The above-mentioned embodiments and modifications are merely examples for performing the present invention, and the present invention is not limited to these embodiments and modifications. In the present invention, a plurality of elements disclosed in the embodiment and each modification can be appropriately combined so as to form various inventions. It is obvious from the above description that the present invention can be variously modified according to a specification or the like, and can further include various other embodiments within a scope of the present invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A guiding device configured to guide a capsule medical device within a subject, the guiding device comprising:
    a magnetic field generator configured to generate a first magnetic field to restrain the capsule medical device at a first restrained position, wherein a range from the first restrained position in which the capsule medical device can be guided by the first magnetic field has a limit distance of a first threshold value;
    a position detector configured to detect a detected position of the capsule medical device in the subject; and
    a controller configured to:
        perform a determination of whether a distance between the first restrained position and the detected position of the capsule medical device is greater than the first threshold value; and
        control the magnetic field generator to generate a second magnetic field to restrain the capsule medical device at a second restrained position closer to the detected position of the capsule medical device than the first restrained position, when the distance is determined to be greater than the first threshold value.

2. The guiding device according to claim 1, further comprising an operation input device configured to receive external operation and to input instruction information for guiding the capsule medical device, into the controller in accordance with the external operation,
wherein the controller is configured to:
switch between a first control mode and a second control mode in accordance with a result of the determination of whether the distance between the first restrained position and the detected position of the capsule medical device is greater than the first threshold value,
wherein in the first control mode, the controller is configured to control the magnetic field generator to generate the second magnetic field to restrain the capsule medical device at the second restrained position closer to the capsule medical device than the first restrained position, and
wherein in the second control mode, the controller is configured to control the magnetic field generator to generate a third magnetic field that guides the capsule medical device based on the instruction information.

3. The guiding device according to claim 2,
wherein the controller is configured to:
execute the second control mode when the distance is determined to be equal to or less than the first threshold value; and
switch from the second control mode to the first control mode when the distance is determined to be greater than the first threshold value.

4. The guiding device according to claim 3,
wherein the controller is configured to switch from the first control mode to the second control mode when the distance is determined to be less than a second threshold value that is smaller than the first threshold value.

5. The guiding device according to claim 3,
wherein the controller is configured to:
execute the second control mode when the distance is determined to be equal to or less than the first threshold value; and
maintain the second control mode when the distance is determined to be greater than the first threshold value while the operation input device is receiving the external operation.

6. The guiding device according to claim 5,
wherein when the distance is determined to be greater than the first threshold value and while the second control mode is maintained, the controller is configured to control a display to display a sign indicating that the distance is greater than the first threshold value.

7. The guiding device according to claim 6,
wherein the controller is configured to:
control the display to display, based on the instruction information, a sign indicating a direction in which the capsule medical device is guidable; and
control the display to change a display mode of the sign depending on which of the first control mode and the second control mode the controller executes.

8. The guiding device according to claim 2,
wherein the magnetic field generator comprises:
a permanent magnet configured to generate the first magnetic field and the second magnetic field; and
a driver configured to change a relative position of the permanent magnet to the capsule medical device,
wherein the controller is configured to control the driver to change the relative position to generate the second magnetic field to restrain the capsule medical device at the second restrained position while executing the first control mode.

9. The guiding device according to claim 2,
wherein the magnetic field generator comprises a plurality of electromagnets,
wherein the controller is configured to control the plurality of electromagnets to generate the second magnetic field to restrain the capsule medical device at the second restrained position.

10. A capsule medical device guiding system comprising:
the guiding device according to claim 1; and
the capsule medical device.

* * * * *